(12) United States Patent
Saadat

(10) Patent No.: US 7,758,571 B2
(45) Date of Patent: Jul. 20, 2010

(54) METHODS AND APPARATUS FOR CRYO-THERAPY

(75) Inventor: Vahid Saadat, Saratoga, CA (US)

(73) Assignee: Nidus Medical, LLC, Saratoga, CA (US)

( * ) Notice: Subject to any disclaimer, the term of this patent is extended or adjusted under 35 U.S.C. 154(b) by 864 days.

(21) Appl. No.: 10/494,487

(22) PCT Filed: Nov. 1, 2002

(86) PCT No.: PCT/US02/35092

§ 371 (c)(1),
(2), (4) Date: Aug. 16, 2004

(87) PCT Pub. No.: WO03/039338

PCT Pub. Date: May 15, 2003

(65) Prior Publication Data

US 2006/0253114 A1    Nov. 9, 2006

Related U.S. Application Data

(60) Provisional application No. 60/350,177, filed on Nov. 2, 2001.

(51) Int. Cl.
*A61B 18/02* (2006.01)
*A61F 7/12* (2006.01)

(52) U.S. Cl. .............................. 606/22; 606/20; 606/21; 606/23; 606/25; 600/585; 607/105

(58) Field of Classification Search ................... 607/96; 606/20–26, 41; 600/585
See application file for complete search history.

(56) References Cited

U.S. PATENT DOCUMENTS

| | | | |
|---|---|---|---|
| 3,452,742 | A | 7/1969 | Muller |
| 3,612,058 | A | 10/1971 | Ackerman |
| 3,918,439 | A | 11/1975 | Zimmer |
| 3,973,556 | A | 8/1976 | Fleischhacker et al. |
| 4,140,109 | A | 2/1979 | Savic et al. |
| 4,202,336 | A | 5/1980 | van Gerven |
| 4,252,130 | A | 2/1981 | Le Pivert |
| 4,327,733 | A | 5/1982 | Gallie |
| 4,483,341 | A | 11/1984 | Witteles |
| 4,528,979 | A | 7/1985 | Marchenko et al. |

(Continued)

FOREIGN PATENT DOCUMENTS

SU   1581294   7/1990

*Primary Examiner*—Roy D Gibson
*Assistant Examiner*—Kaitlyn E Helling
(74) *Attorney, Agent, or Firm*—Levine Bagade Han LLP

(57) ABSTRACT

Methods and apparatus for cryo-therapy are disclosed herein. This includes a hollow guidewire disposed within a catheter having helical loops contacting tissue. A coolant delivery tube disposed within can have a coolant delivered from a proximal end into the guidewire lumen. The coolant flows back proximally through the guidewire while cooling the guidewire surface and cooling or cryogenically ablating the contacting tissue. To minimize guidewire exposure to surrounding fluids or tissue, insulative barriers can be attached to the guidewire. A coolant delivery tube and return lumen can be integrated from a single extrusion in various configurations. Expandable balloons can also be used to expand the loops of the guidewire to contact the tissue. Also, helical loops with a coolant delivery tube or stem disposed longitudinally within the loops can be used and the loops can also have a variable collapsible cooling region.

36 Claims, 10 Drawing Sheets

U.S. PATENT DOCUMENTS

| | | | |
|---|---|---|---|
| 4,621,635 A | 11/1986 | Ali | |
| 4,690,155 A | 9/1987 | Hess | |
| 4,699,147 A | 10/1987 | Chilson et al. | |
| 4,709,698 A | 12/1987 | Johnston et al. | |
| 4,719,924 A * | 1/1988 | Crittenden et al. | 600/585 |
| 4,754,752 A | 7/1988 | Ginsburg et al. | |
| 4,776,349 A | 10/1988 | Nashef et al. | |
| 4,790,813 A * | 12/1988 | Kensey | 604/22 |
| 4,860,744 A | 8/1989 | Johnson et al. | |
| 4,884,573 A * | 12/1989 | Wijay et al. | 606/194 |
| 4,945,912 A | 8/1990 | Langberg | |
| 4,946,440 A | 8/1990 | Hall | |
| 4,946,466 A * | 8/1990 | Pinchuk et al. | 606/194 |
| 4,953,553 A * | 9/1990 | Tremulis | 600/486 |
| 4,979,948 A | 12/1990 | Geddes et al. | |
| 4,998,933 A | 3/1991 | Eggers et al. | |
| 5,007,437 A | 4/1991 | Sterzer | |
| 5,010,894 A | 4/1991 | Edhag | |
| 5,078,713 A | 1/1992 | Varney | |
| 5,100,388 A | 3/1992 | Behl et al. | |
| 5,108,390 A | 4/1992 | Potocky et al. | |
| 5,139,496 A | 8/1992 | Hed | |
| 5,147,355 A | 9/1992 | Friedman et al. | |
| 5,224,943 A | 7/1993 | Goddard | |
| 5,228,442 A | 7/1993 | Imran | |
| 5,231,995 A | 8/1993 | Desai | |
| 5,281,213 A | 1/1994 | Milder et al. | |
| 5,281,215 A | 1/1994 | Milder | |
| 5,293,869 A | 3/1994 | Edwards et al. | |
| 5,334,181 A | 8/1994 | Rubinsky et al. | |
| 5,342,295 A | 8/1994 | Imran | |
| 5,403,309 A | 4/1995 | Coleman et al. | |
| 5,423,807 A | 6/1995 | Milder | |
| 5,425,711 A * | 6/1995 | Ressemann et al. | 604/103.1 |
| 5,452,582 A | 9/1995 | Longsworth | |
| 5,487,385 A | 1/1996 | Avitall | |
| 6,129,724 A * | 10/2000 | Fleischman et al. | 606/41 |
| 6,139,570 A | 10/2000 | Saadat et al. | |
| 6,161,543 A * | 12/2000 | Cox et al. | 128/898 |
| 6,241,722 B1 * | 6/2001 | Dobak et al. | 606/23 |
| 6,270,476 B1 | 8/2001 | Santoianni et al. | |
| 6,270,493 B1 | 8/2001 | Lalonde et al. | |
| 6,554,797 B1 * | 4/2003 | Worthen | 604/113 |
| 6,607,520 B2 * | 8/2003 | Keane | 606/2 |
| 2003/0009875 A1 | 1/2003 | Saadat | |
| 2003/0013983 A1 | 1/2003 | Saadat | |
| 2003/0013984 A1 | 1/2003 | Saadat | |
| 2003/0013985 A1 | 1/2003 | Saadat | |
| 2003/0013986 A1 | 1/2003 | Saadat | |
| 2003/0013987 A1 | 1/2003 | Saadat | |
| 2007/0250050 A1 | 10/2007 | Lafontaine | |

* cited by examiner

METHODS AND APPARATUS FOR CRYO-THERAPY

CROSS-REFERENCE TO RELATED APPLICATIONS

This application claims the benefit of U.S. Provisional Patent Application No. 60/350,177, entitled "Methods and Apparatus for Cryo-Therapy" filed Nov. 2, 2001, and U.S. patent application Ser. No. 10/010,399, entitled "Methods and Apparatus for Cryo-Therapy" filed Dec. 5, 2001, now abandoned.

TECHNICAL FIELD OF THE INVENTION

The present invention relates to cryo-therapy. More particularly, the present invention relates to methods and apparatus for endovascularly cooling and/or freezing preselected regions of tissue.

BACKGROUND ART OF THE INVENTION

Acute ischemic syndromes involving arterial blood vessels, such as myocardial infarction, or heart attack, and stroke, frequently occur when atherosclerotic plaque ruptures, triggering the formation of blood clots, or thrombosis. Plaque that is inflamed is particularly unstable and vulnerable to disruption, with potentially devastating consequences. Therefore, there is a strong need to detect and locate this type of plaque so that treatment can be initiated before the plaque undergoes disruption and induces subsequent life-threatening clotting.

Researchers, acting on the theory that inflammation is a factor in the development of atherosclerosis, have discovered that local variations of temperature along arterial walls can indicate the presence of inflamed plaque. The temperature at the site of inflammation, i.e., the unstable plaque, is elevated relative to adjacent plaque-free arterial walls.

Using a tiny thermal sensor at the end of a catheter, the temperature at multiple locations along an arterial wall were measured in people with and without atherosclerotic arteries. In people free of heart disease, the temperature was substantially homogeneous wherever measured: an average of 0.65° F. (0.36° C.) above the oral temperature. In people with stable angina, the temperature of their plaques averaged 0.19° F. (0.11° C.) above the temperature of their unaffected artery walls. The average temperature increase in people with unstable angina was 1.23° F. (0.68° C.). The increase was 2.65° F. (1.47° C.) in people who had just suffered a heart attack. Furthermore, temperature variation at different points at the plaque site itself was found to be greatest in people who had just had a heart attack. There was progressively less variation in people with unstable angina and stable angina.

The temperature heterogeneity discussed above can be exploited to detect and locate inflamed, unstable plaque through the use of cavity wall profiling apparatus. Once located, treatment can then be initiated upon the inflamed, unstable plaque region.

One such method of treatment involves cryo-therapy in which regions of tissue may be cooled to temperatures as low as −112° F. (−80° C.) by catheters inserted endovascularly into a patient. This form of treatment delivers energy to ablate the tissue in a manner which is generally safer and more effective than other conventional methods of treatment.

Various conventional endovascular catheters used for freezing, heating, or ablating tissue are well known. Certain catheters used for cooling and/or freezing typically employ one of several methods. One such method takes advantage of cooling by use of a phase change refrigerant which may enter a patient's body at ambient temperature and attains cooling by expansion within a cooling chamber disposed within the catheter body located at the selected treatment site. The wall of the cooling chamber is typically placed in contact with adjacent tissue to effect conduction cooling or ablation.

Another method involves utilizing the expansion of a phase change or high pressure coolant exiting from a nozzle within the catheter tip to create a highly turbulent flow region.

However, problems exist with conventional cooling and cryo-treatment devices. One such problem is that conventional devices usually exert an undue amount of force on the region of interest. If the region of interest cannot withstand these forces, it may be damaged. The inside walls of a healthy human artery are vulnerable to such damage. Furthermore, if inflamed, unstable plaque is present it may be ruptured by such forces.

Another problem with conventional devices is that they can only treat tissue at one specific location. In order to treat an entire tissue region of interest, one would need to move the cooling apparatus from location to location. If the cooling apparatus were placed on an angioplasty balloon, for instance, the balloon would need to be deflated, placed at the desired location, inflated and placed in contact with the tissue, and cooled, and so on for each treatment location. This can be very tedious, can increase the risk of damaging the vessel wall or rupturing vulnerable plaque, and may not treat the entire region of tissue.

Accordingly, there exists a need for a device which is able to cryogenically treat a predetermined region of tissue, such as a region of unstable plaque, efficiently and effectively without damaging the surrounding and underlying tissue.

SUMMARY OF THE INVENTION

Cryo-therapy of tissue involves many different device variations and methods. One variation involves having a hollow ablating tool or a hollow guidewire configured to form multiple loosely spaced helical loops. The guidewire itself may be formed of a thin wire wound into small helical coils of a predetermined diameter that may lie tightly adjacent to one another forming a central passageway. The guidewire may have a first straightened configuration when constrained within a catheter and a second relaxed configuration self-forming or springing into the helical loops upon being removed from the catheter. Accordingly, the guidewire may be made of a material such as spring steel or a superelastic alloy with shape memory characteristics, e.g., nitinol.

In this variation, the device may be advanced to a region of tissue to be cryogenically treated and the helical loops may be withdrawn to radially extend into contact with the targeted tissue. Within the hollow guidewire, a coolant delivery tube may be disposed to extend entirely to the distal end of the guidewire or near the distal end. Alternatively, the coolant delivery tube may be anchored to the distal end of the guidewire. Within the delivery tube, a coolant or refrigerant may be pumped from a proximal end, either by a positive or negative pressure pump and regulator located proximally. The delivered coolant may pass into the guidewire lumen through one or multiple delivery ports defined along the delivery tube surface at or near the delivery tube distal end. Once the coolant passes into the guidewire lumen, it may travel proximally through the guidewire while cooling the guidewire surface and subsequently cooling or cryogenically ablating the contacting tissue.

After the desired tissue has been treated, the guidewire may be withdrawn into the catheter and the catheter assembly moved to the next treatment site. Alternatively, the guidewire may be slowly withdrawn into the catheter while the catheter is held stationary relative to the tissue; the guidewire in this case may cool or ablate the tissue while in motion, i.e., while being deployed or withdrawn.

The tip or cap of the guidewire may be made of a thermally conductive material, such as stainless steel or nitinol, to effect a specified contacting region for treatment of the tissue. Also, a lining or elastic membrane capable of withstanding low temperatures may be disposed over the guidewire, either within the guidewire lumen or on an outer surface of the guidewire to help contain the coolant within the device. The refrigerant or coolant used may be in either liquid or gas form and may include a number of different chemicals and compounds such as nitrogen, nitrous oxide, carbon dioxide, chilled saline, fluorinated hydrocarbon (Fluorinert™), and liquid chlorodifluoromethane, among others.

Alternatively, a coolant having a low boiling point may be used to allow delivery through a delivery tube in a liquid form. Once this coolant is pumped into the guidewire lumen, by virtue of the heat transferred from the surrounding tissue, blood, or fluid around the guidewire, the liquid coolant may undergo a phase transition into a gas and subsequently be pumped back proximally through the guidewire lumen while cooling the guidewire. Another alternative is to pass the coolant through a valve located at the distal end of the delivery tube. As the coolant passes through the valve, it expands into a cooling gas by what is known as the Joule-Thompson effect. Fluids such as nitrogen, nitrous oxide, or carbon dioxide may be suitable for such a mode of heat transfer.

To minimize the exposure of the guidewire to blood, fluids, or other tissue, insulative barriers or shingles may be attached to at least a portion of the loops to help insulate the guidewire. Reducing the heat transfer area of the guidewire to tissue or blood not being treated may aid in optimizing the efficiency of the coolant during treatment.

Different variations on the guidewire itself may be utilized to efficiently cool or ablate tissue. For instance, a guidewire may have both a coolant delivery tube and expansion or coolant return lumen integrated from a single extrusion. Alternatively, separate delivery tubes may be integrated with a coolant expansion/return lumen to form an integral tubular structure. Other variations may include having a central coolant delivery lumen surrounded by a plurality of insulating and coolant return lumens. Conduction members may optionally be embedded into the wall of the guidewire such that the conduction members contact the coolant to effect a thermal circuit for optimal heat transfer.

Different modes of deployment may also be utilized. The guidewire may simply be withdrawn from the catheter and left to self-form or radially extend until it contacts the tissue walls. But expansion devices such as expandable balloons, e.g., angioplasty balloons, may be utilized by placing one within the loops of the guidewire and expanding it to move the loops of the guidewire into contact with the tissue. Once contact is achieved, the balloon may be deflated and removed from the area. Also, the helical loops of a guidewire may also be integrally formed in, e.g., a bilayered balloon having an integrated return channel or lumen for the spent coolant to pass through. Such an expandable balloon preferably has a throughpath or flowthrough channel which would allow blood or other fluids to continue flowing uninterrupted through the vasculature.

Furthermore, self-forming helical loops may also be utilized with a coolant delivery tube or stem disposed longitudinally within the loops. This device may be rotatably withdrawn or advanced through a catheter as a unit and may facilitate placement of the device upon the region of tissue to be treated. And other variations also may be used which have a variable collapsible cooling region. Such a cooling region may be manipulated at its proximal end to concentrate or disperse the heat transfer area contacting the targeted tissue depending upon the desired mode of treatment.

DETAILED DESCRIPTION OF THE INVENTION

Figure 1:
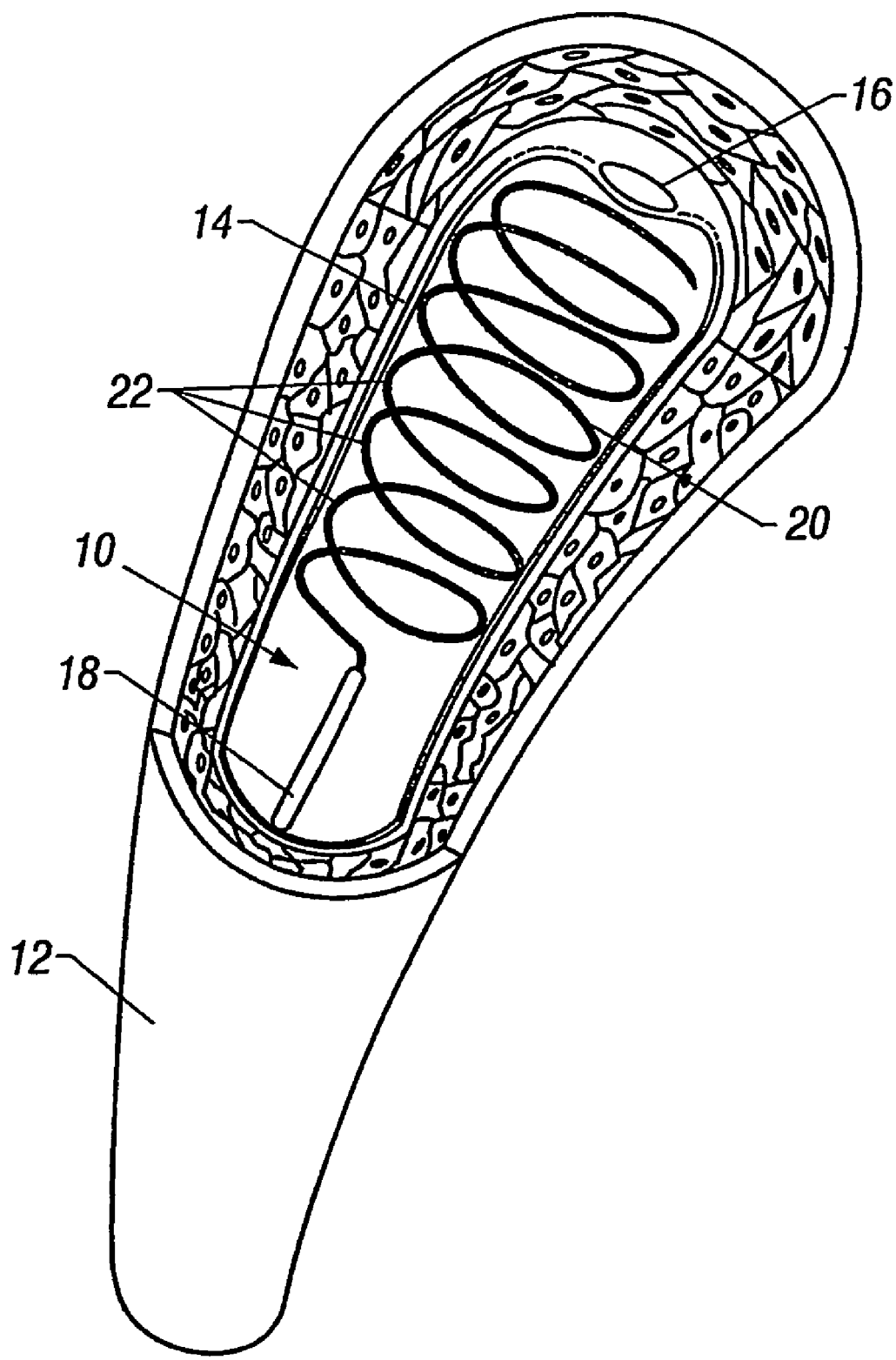
FIG. 1 shows a cryo-therapy device positioned within an arterial blood vessel with several helical guidewire loops deployed.

Cryogenic treatment of tissue may involve many different device variations and methods. As shown in FIG. 1, cryotherapy device 10 is shown positioned within arterial blood vessel 12, which has its wall partially removed for clarity. One variation of the device 10 is shown as having a hollow guidewire 20 configured to form multiple loosely spaced helical loops 22. Guidewire 20 is preferably made of a thin wire which may be wound into small helical coils of a predetermined diameter that may lie tightly adjacent to one another to form a hollow guidewire 20 defining a central passageway. These loops 22 may be held within lumened catheter 18 in a first configuration while being delivered to the desired treatment site.

Once ejected or pushed from catheter 18, guidewire 20 may be self-deploying or self-forming such that when it is unconstrained, it reconfigures itself into a second configuration. This may be accomplished by having guidewire 20 self-form or spring into helical loops 22 upon being removed from catheter 18 or guidewire 20 may form into helical loops 22 upon exposure to the vessel 12 environment. Accordingly, guidewire 20 may be formed from a metal such as spring steel that can be deformed into a first straight configuration to spring into a second looped configuration when withdrawn from catheter 18. Guidewire 20 may alternatively be made from a superelastic metal, such as nitinol, which may automatically form into the looped configuration from a straight one upon withdrawal from catheter 18. Furthermore, guidewire 20 may also be made from a superelastic metal, again such as nitinol having shape memory alloy characteristics. Thus, guidewire 20 may be initially inserted through catheter 18 at an initial lower temperature, e.g., by injecting cold saline solution over guidewire 20. Upon withdrawal from catheter 18 within the body lumen of vessel 12, the ambient heat from the surrounding environment such as the blood or tissue may transform guidewire 20 into helical loops 22.

Guidewire 20 may also be made from a composite such as a nitinol tube disposed within the guidewire structure. In this manner, the martensitic or superelastic properties of nitinol may be combined with spring steel characteristics. Guidewire 20 may also be made from other biocompatible materials such as copper, constantan, chromel, or alumel.

As further seen in FIG. 1, once guidewire 20 is withdrawn from catheter 18, the helical loops 22 preferably reconfigure themselves such that they extend radially to come into gentle contact with the inner wall or endothelium 14 of vessel 12. Helical loops 22 are preferably positioned within vessel 12 such that they come into contact with a location of the tissue to be treated, such as plaque 16. Once the desired region of treatment, such as plaque 16, is contacted or in close proximity to guidewire 20, the cryogenic treatment may be effected by cryotherapy device 10. After the desired tissue has been treated, guidewire 20 may be withdrawn and catheter 18 may be moved to the next treatment site. Alternatively, guidewire 20 may be slowly withdrawn into catheter 18 while catheter 18 is held stationary relative to the tissue; guidewire 20 in this case may cool or ablate the tissue while in motion, i.e., while being deployed or withdrawn.

Variations of the guidewire 20 as well as various methods and devices for sensing and measuring characteristics of regions of tissue, such as plaque 16, are discussed in further detail in each of the following U.S. patent applications. Each application is currently co-pending, have all been filed on Jul. 12, 2001, and are all incorporated herein by reference in their entirety: U.S. patent application Ser. No. 09/904,012 entitled "Expandable Device for Sensing Temperature Profile of a Hollow Body Organ"; U.S. patent application Ser. No. 09/904,080 entitled "Method for Sensing Temperature Profile of a Hollow Body Organ"; U.S. patent application Ser. No. 09/904,212 entitled "Device for Sensing Temperature Profile of a Hollow Body Organ"; U.S. patent application Ser. No. 09/904,024 entitled "Method for Sensing and Mapping Temperature Profile of a Hollow Body Organ"; U.S. patent application Ser. No. 09/903,960 entitled "Method for Mapping Temperature Profile of a Hollow Body Organ"; U.S. patent application Ser. No. 09/904,220 entitled "Expandable Device for Mapping Temperature Profile of a Hollow Body Organ".

Figure 2:
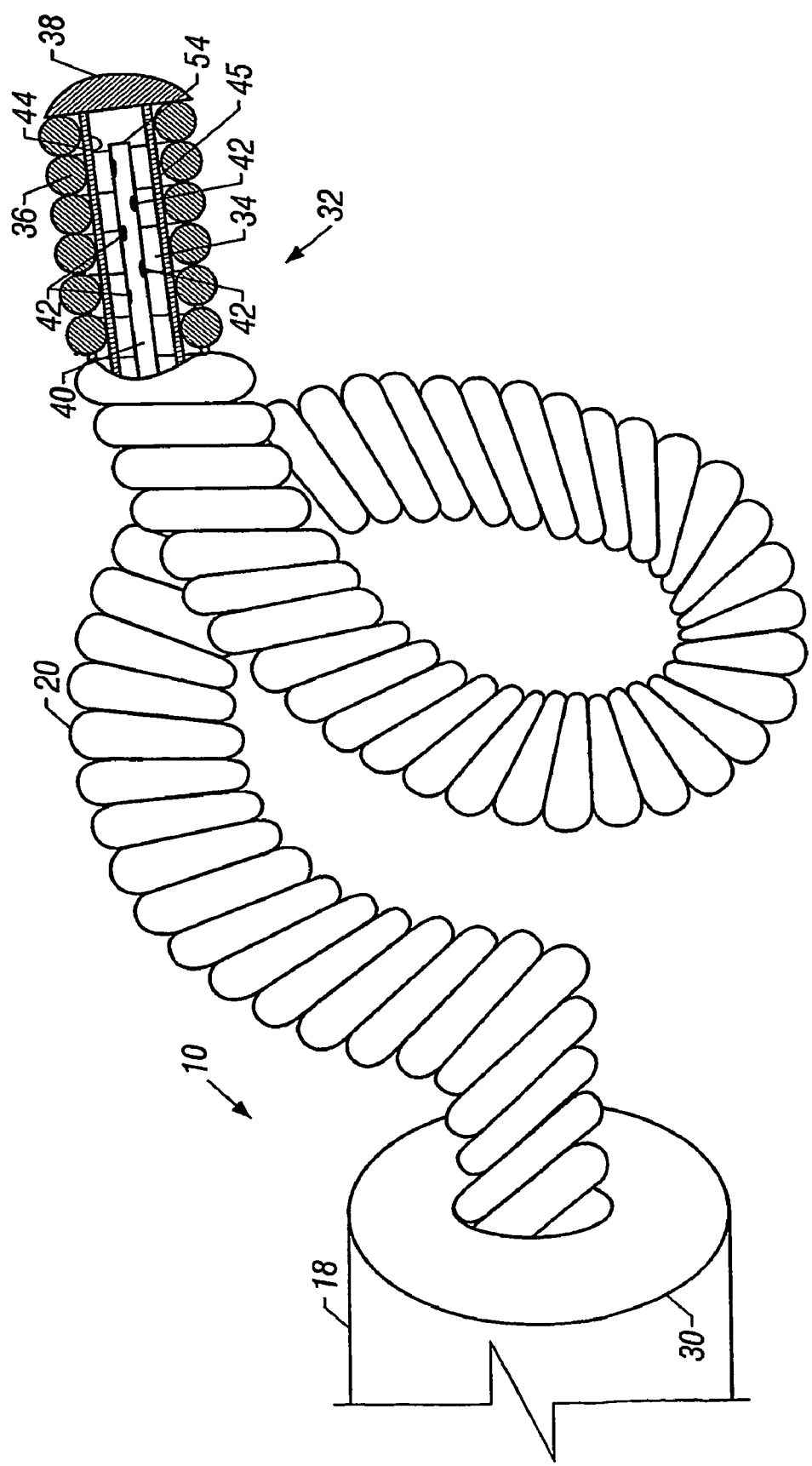
FIG. 2 shows a representative side view of a variation of the cryo-therapy device with the guidewire partially withdrawn.

FIG. 2 shows a close-up representation of guidewire 20 partially withdrawn from catheter 18. Guidewire 20 has been partially extended from catheter 18 through lumen 30. Catheter 18 may have multiple access lumens through which a variety of devices, e.g., temperature profiling devices, optical devices, etc., may be accessible, although a single lumen 30 is presently shown. The guidewire distal end 32 is shown partially removed for clarity to reveal a variation of the cooling structure. As seen, guidewire 20 may be formed by wound wire 36 such that guidewire lumen 34 is defined within. A cap or tip 38 may be placed at the distal end of guidewire 20 to cover guidewire lumen 34 and may be made of a variety of biocompatible conductive materials, such as stainless steel or nitinol. Cap 38 may also be made of a variety of polymeric materials capable of withstanding low temperatures.

In this variation, coolant delivery tube 40 may be placed at least partially within guidewire lumen 34. Tube 40 preferably extends throughout the length of lumen 34 such that the distal end 54 of delivery tube 40 is just proximal of cap 38. A lining or elastic membrane 44 may be formed to cover the inner surface of wire 36 and held by, e.g., an adhesive 45, to ensure that coolants or refrigerants flowing within guidewire 20 are fully contained within. Membrane 44 may be made of various materials capable of withstanding low temperatures, e.g., silicone, polyethylene (PE), fluoroplastics such as polytetrafluoroethylene (PTFE), fluorinated ethylene polymer (FEP), perfluoroalkoxy (PFA), and thermoplastic polymers, such as polyurethane (PU), etc. The distal section of delivery tube 40 may have at least one delivery ports 42 and preferably a number of ports 42 spaced along the distal length. A refrigerant or coolant may be pumped from a proximal end of delivery tube 40 down to its distal end such that the coolant passes through delivery ports 42 near the guidewire distal end 32. The coolant pumped into guidewire lumen 34 through delivery ports 42 may then be channeled back through to the proximal end of guidewire 20 and catheter 18 meanwhile cryogenically cooling the guidewire 20 surface which subsequently cools or ablates the targeted tissue which guidewire 20 contacts. Delivery tube 40 may be inserted into guidewire lumen 34 and deployed within vessel 12 either with guidewire 20 or it may be inserted separately into lumen 34 after guidewire 20 has already been deployed. Accordingly, lumen 34 may be used for other purposes as well, e.g., holding a temperature sensing device for measuring the temperature of the wall of vessel 12 prior to the cryogenic treatment.

To regulate the coolant pumped through device 10, a regulator (not shown) connected to the proximal end of device 10 may be used to control the amount of pressure within the coil. A positive pressure pump may be used to deliver the coolant through device 10 via tube 40, but a negative pressure pump may also be used to draw the coolant through guidewire lumen 34. Use of negative pressure may also aid in ensuring that excess coolant does not escape into a patient's body if a leak or failure in the structure of guidewire 20 were to ever occur.

The refrigerant or coolant used may variously be in liquid, gas, or mixed form and may include a number of different chemicals and compounds such as nitrogen, nitrous oxide, carbon dioxide, chilled saline, Fluorinert™, and liquid chlorodifluoromethane, among others. Alternatively, a coolant having a low boiling point may be used to allow delivery through tube 40 in liquid form. Once this coolant is pumped into guidewire lumen 34, by virtue of the heat transferred from the surrounding tissue, blood, or fluid around guidewire 20 and/or by the rapid expansion of the coolant, the liquid coolant may undergo a phase transition into a gas and subsequently be pumped back proximally through lumen 34 while cooling guidewire 20. The coolant may also be passed through a valve 51 located at the distal end of delivery tube 40. As the coolant passes through valve 51, it may expand into a cooling gas by what is known as the Joule-Thompson effect and this gas may be used to cool the device and ablate the tissue. Temperatures which may be used to effect the desired results may be as low as 14° F. to 41° F. (−10° C. to 5° C.), or even lower. Fluids such as nitrogen or nitrous oxide may be suitable for such a mode of heat transfer. Accordingly, tube 40 is preferably formed of a metal or polymeric material capable of withstanding extremely low temperatures. Such materials may include metals such as nitinol and stainless steel, as well as polymers such as silicone, PE, PTFE, FEP, PFA, and thermoplastic polymers, such as PU, etc.

To determine the preferable flow rates of the coolant through guidewire 20 to have effective cooling and tissue treatment, as well as the amount of heat transfer necessary for cooling the tissue, a standard equation for calculating convective heat transfer from the tissue may be used. The equation (1) is shown below:

$$q_c = h_c A (T_1 - T_2) \quad (1)$$

where, $q_c$=the heat transferred from the contacting tissue; $h_c$=the convection heat transfer coefficient; A=the surface area the coolant is exposed to; $T_1$ and $T_2$ represent the temperature differences through the various media which the heat is transferred.

Figure 3A:
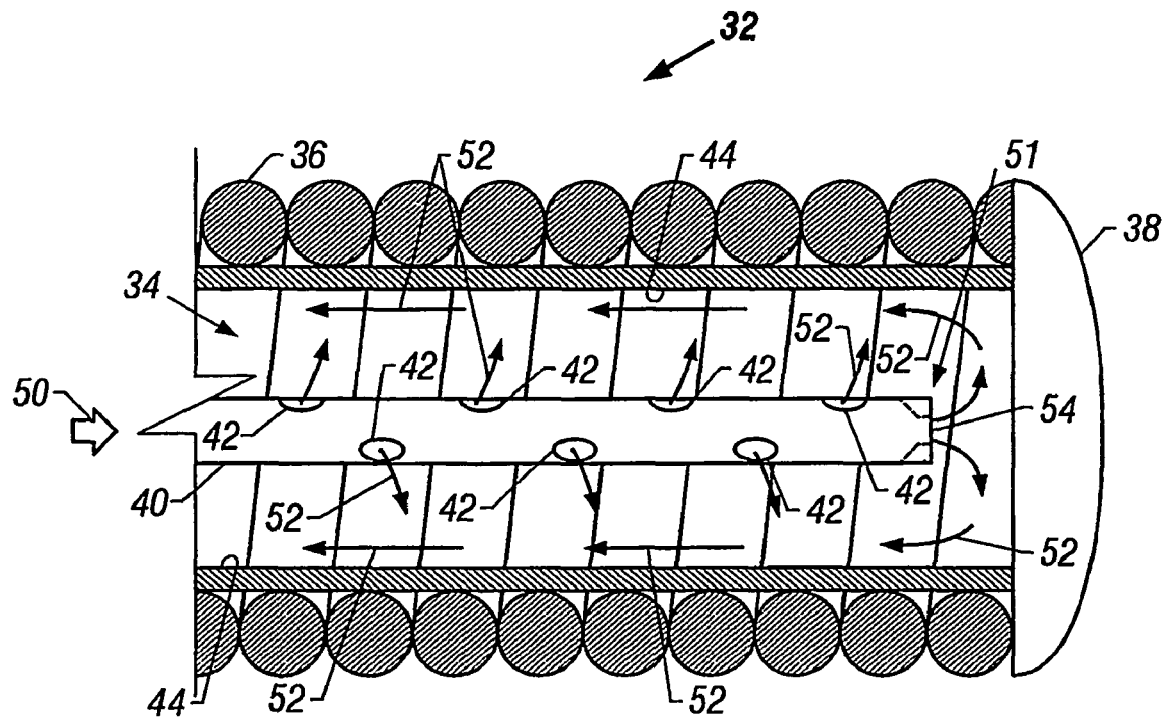
FIG. 3A shows a detailed cross-sectional side view of a variation on the guidewire distal end.

Various methods of coolant delivery may be employed. For instance, FIG. 3A shows one variation of a detailed cross-sectional view of guidewire distal end 32 from FIG. 2. As seen, delivery tube 40 may be disposed within guidewire lumen 34 such that the delivery tube distal end 54 is located in apposition to cap 38. As coolant is pumped in 50 through tube 40, it may optionally pass through delivery ports 42 and/or delivery tube distal end 54. The coolant flow 52 may then be passed proximally back through guidewire lumen 34. For a given device, such as that shown in FIG. 2 as device 10, the coolant flowing through delivery tube 40 may have a flow rate of about 40 cm³/min. (cc/min.) to drop the temperature to an effective level for treatment. As coolant 52 passes over membrane 44 and wire 36, coolant 52 becomes spent while transferring heat and lowering the temperature of wire 36. Cap 38 may also be made of thermally conductive materials such as biocompatible metals like stainless steels. A thermally conductive cap 38 may aid in cooling the cap 38 temperature to allow for direct or selective tissue ablation via cap 38. Delivery tube 40 may also be selectively placed within guidewire lumen 34 such that cooling of selective portions of guidewire 20 occurs where the delivery tube distal end 54 is located.

Figure 3B:
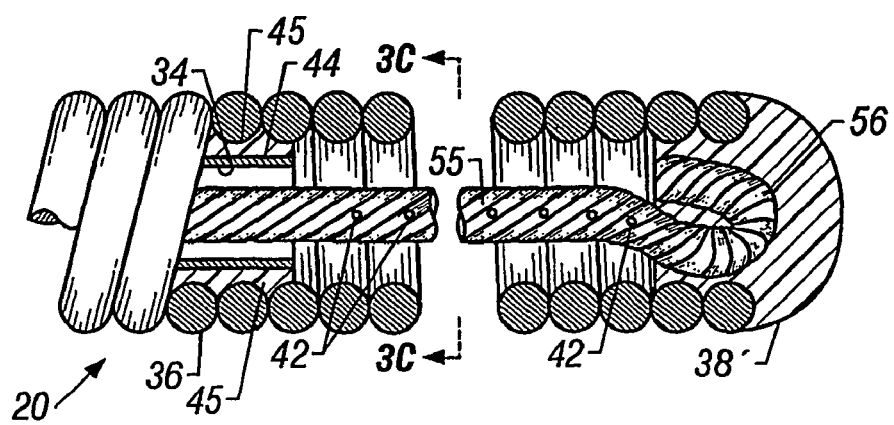
FIG. 3B shows a detailed cross-sectional side view of another variation on the guidewire distal end.
Figure 3C:
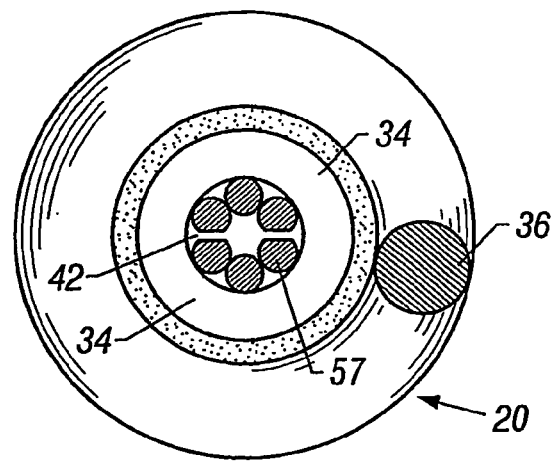
FIG. 3C shows cross-section 3C-3C of the variation from FIG. 3B.

Another variation on the guidewire distal end 32 is seen in FIGS. 3B and 3C. FIG. 3B shows a cross-sectioned side view of an alternative coolant delivery method. An anchored coolant delivery tube 55 may be disposed within lumen 34 of guidewire 20. Delivery tube 55 may have an anchoring end 56 which may be formed integrally with anchoring cap 38' or by a variety of other methods. Having anchoring end 56 formed with cap 38' may facilitate the cooling of cap 38' if coolant is channeled through tube 55. Delivery tube 55 may be formed of a polymeric tube capable of withstanding low temperatures for extended periods of time. Alternatively, tube 55 may be formed of wound wire strands 57 forming a hollow central lumen through which the coolant may be delivered, as seen in FIG. 3C which is the cross-section 3C-3C taken from FIG. 3B. Coolant may be delivered through delivery ports 42 such that the coolant contacts wire 36 and is passed proximally through guidewire lumen 34 subsequently cooling the guidewire 20 as the coolant passes through.

Figure 3D:
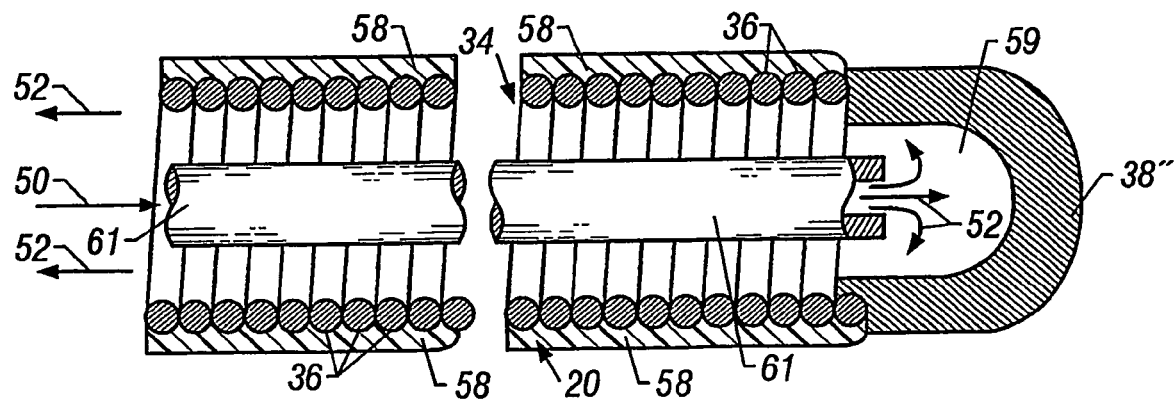
FIG. 3D shows a detailed cross-sectional side view of another variation on the guidewire distal end.

FIG. 3D shows another variation on the guidewire distal end 32. As shown, an elastic membrane or coating 58 may be applied exteriorly of wound wire 36. Membrane 58 is preferably made of any of the polymeric materials described above which are capable of withstanding low temperatures and may be placed exteriorly of wire 36 to aid with the lubricity of the device as well as containing the coolant within guidewire lumen 34. In this variation, coolant delivery tube 61 may be disposed within guidewire lumen 34 such that coolant 50 delivered therethrough would exit the tube 61 distal end, as shown by exiting coolant 52, at expansion region 59 and preferably in contact with expanded cap 38". In this variation, expanded cap 38" may be made of a thermally conductive material, e.g., stainless steel, such that cooling may be facilitated and cap 38" may be used for selective tissue contact and ablation. Although delivery tube 61 is shown with coolant 52 exiting the distal tip portion to expand in expansion region 59 and effectively cool cap 38", tube 61 may also have delivery ports defined in its walls as in the other variations described above.

Figure 3E:
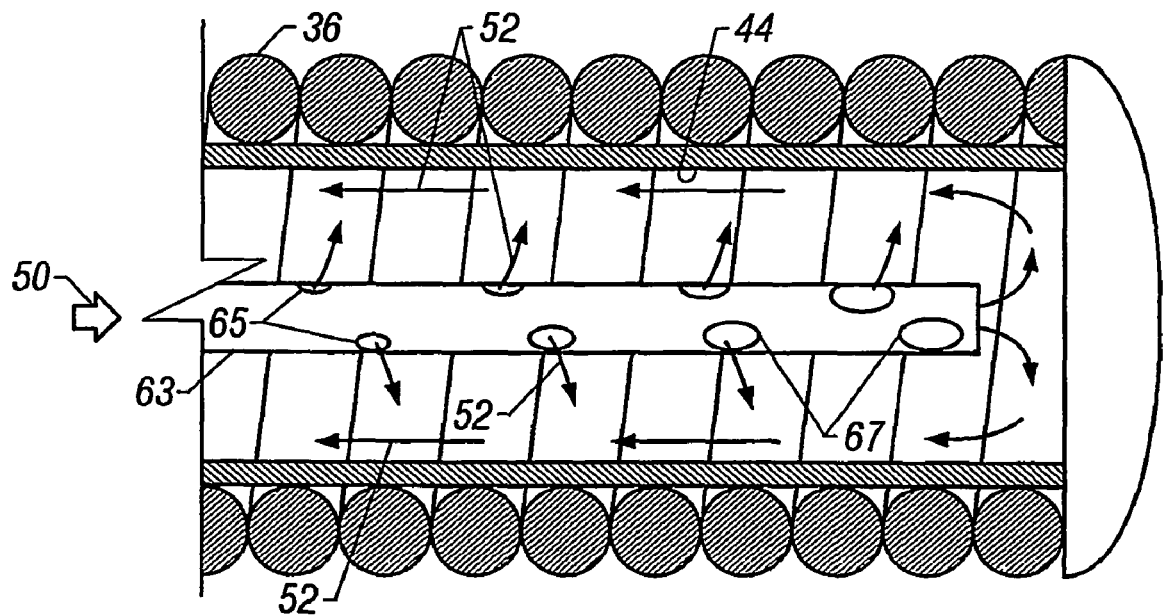
FIG. 3E shows a detailed cross-sectional side view of yet another variation on the guidewire distal end having variable coolant delivery ports.

FIG. 3E shows yet another variation on the guidewire distal end 32. This variation is similar to that shown in FIG. 3A, but coolant delivery tube 63 may have delivery ports of variable sizes and diameters. As shown, delivery ports 65 located closer towards the proximal end of delivery tube 63 may have diameters which are relatively smaller than the diameters of distally located delivery ports 67. The farther distally delivery ports 67 are located, the larger they may become in diameter relative to proximal delivery ports 65 to aid in the distribution of passing coolant 52 under even pressure throughout the guidewire.

Figure 4:
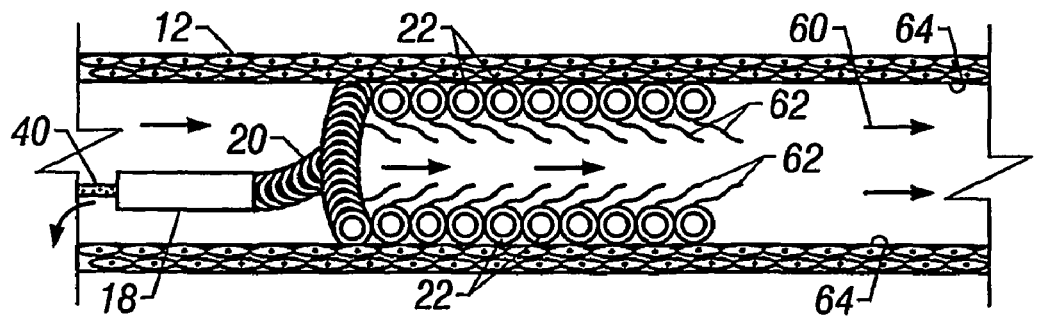
FIG. 4 shows a variation on the cryo-therapy device having insulative barriers attached to the guidewire.

Measures may be taken to optimize the heat transfer between the tissue and the guidewire while minimizing heat transfer to other parts of the body during treatment. As seen in the cross-section of FIG. 4, hollow guidewire 20 with coolant delivery tube 40 disposed within is shown withdrawn from catheter 18 and forming helical loops 22 in contact with inner wall 64 of vessel 12. While loops 22 are in contact with vessel wall 64, the contacted area may be ablated by the cooled loops 22. However, the blood 60 flowing past the loops 22 may also be cooled, thereby reducing the efficiency of the coolant in ablating the tissue since the heat transfer is occurring over a larger area of the loops 22. Thus, insulative barriers or shingles 62 may be attached to a portion of the loops 22 facing the blood flow 60. Barriers 62 may be attached over the entire exposed loops 22 facing the blood flow 60, as shown, or over portions of loops 22 and may be made of a variety of compressible, thermally insulative materials preferably deliverable through a catheter 18. Such materials may include any of the polymers described above, e.g., silicone, polyethylene (PE), fluoroplastics such as polytetrafluoroethylene (PTFE), fluorinated ethylene polymer (FEP), perfluoroalkoxy (PFA), and thermoplastic polymers, such as polyurethane (PU), etc.

Figure 5A:
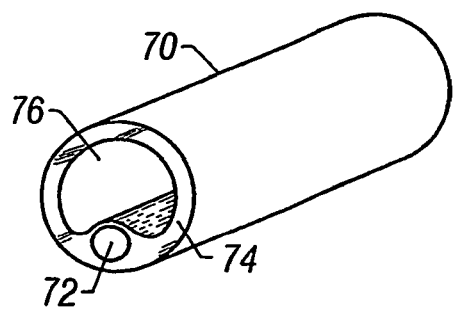
FIG. 5A shows an isometric view of a representative section of a variation on the tubing for delivering coolant.

Other variations of the guidewire coil itself may be used to deliver coolants and refrigerants therethrough. Rather than having a separate coolant delivery tube disposed within a hollow guidewire coil, a variation of the guidewire coil shown in FIGS. 5A and 5B may alternatively be used. As seen in FIG. 5A, the wire used to form the hollow guidewire may itself be formed from a single extrusion shown in the representative section of delivery tube 70. Such a tube may be made of a variety of materials capable of withstanding low temperatures, e.g., stainless steel, nitinol, etc. Alternatively, a slightly larger version of the integral delivery tube 70 may be formed directly into the helical loops. In either case, such a tube 70 is preferably a single-piece tube having a coolant lumen 72 and an expansion lumen 76 formed integrally within tube wall 74.

Figure 5B:
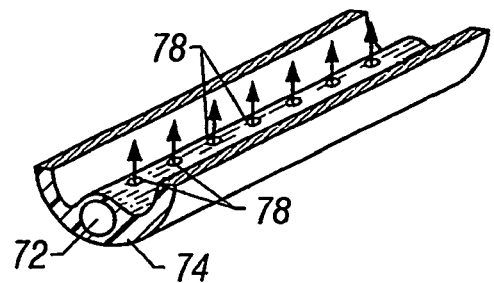
FIG. 5B shows a longitudinal cross-section of the interior of the tubing from FIG. 5A.

FIG. 5B shows a longitudinally cross-sectioned view of the interior of integral delivery tube 70. Coolant delivery ports 78 defined along coolant lumen 72 may place coolant lumen 72 in fluid communication with expansion lumen 76. In operation, coolant delivered through lumen 72 may pass or expand through delivery ports 78 into expansion lumen 76, where the larger surface area may be utilized to effect a more efficient heat transfer. Delivery ports 78 may be positioned at predetermined locations along coolant lumen 72 such that when tube 70 is formed into helical loops, the contact between tube 70 and the desired region of tissue for treatment is optimized.

Figure 6:
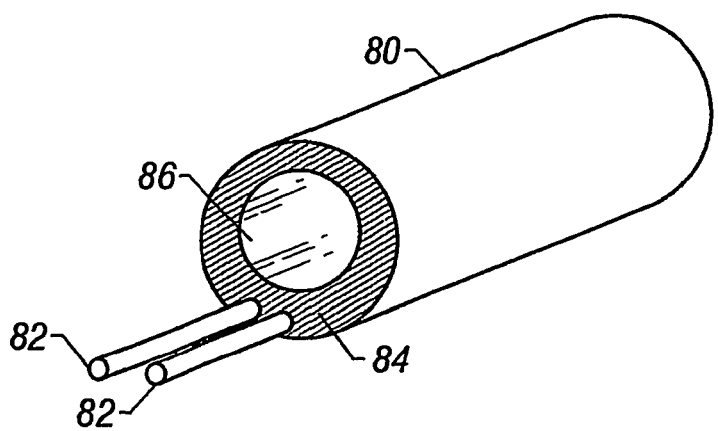
FIG. 6 shows another variation on the tubing for delivering coolant.

FIG. 6 shows another variation of the guidewire coil in the isometric view of a section of tube 80. In this variation, tube 80 may be formed over separate integral delivery tubes 82 formed within tube wall 84. Delivery tubes 82 may be formed from separately extruded wires or tubes and then tubing wall 84 may be formed with delivery tubes 82. As above, delivery tubes 82 may be used to deliver coolant for expansion and/or return through expansion/return lumen 86. Alternatively, delivery tubes 82 may be used to complete a circuit of delivered and returning spent coolant while lumen 86 may be used as an access channel for other applications and devices. Separate expansion lumen 86 is preferably formed integrally within tube 80 in this variation.

Figure 7:
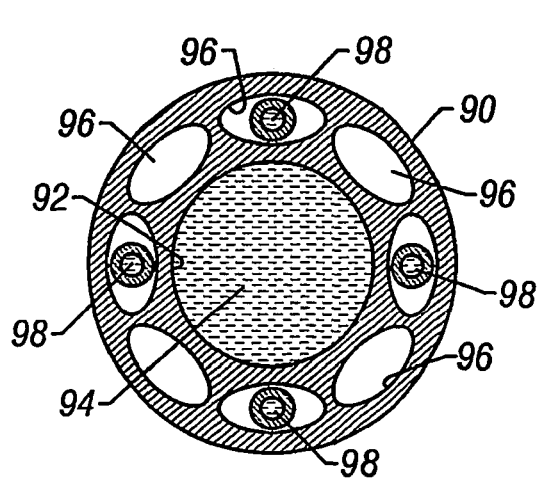
FIG. 7 shows a cross-sectioned view of another variation on the tubing for delivering coolant.

Another alternative variation for a guidewire coil is shown in FIG. 7. Here, a representative cross-section of guidewire 90 is seen having coolant 94 delivered through coolant delivery lumen 92. There may be any number of additional lumens 96 having smaller diameters than lumen 92 and surrounding delivery lumen 92, as shown. Guidewire 90 in this variation may be extruded to form an integral wire or tubing having the number of different channels. Additional lumens 96 may be filled with air or they may be evacuated to provide additional insulation as coolant 94 is delivered through guidewire 90. The coolant may be channeled back to the proximal end of guidewire 90 by any number of coolant return lines 98, which may be located within at least some of lumens 96 or the coolant may be channeled back directly within lumens 96. As the coolant is returned to the proximal end of guidewire 90, cooling at the distal end and along the outer surface of the guidewire 90 may be effected to treat contacting tissue, as described above.

Figure 8:
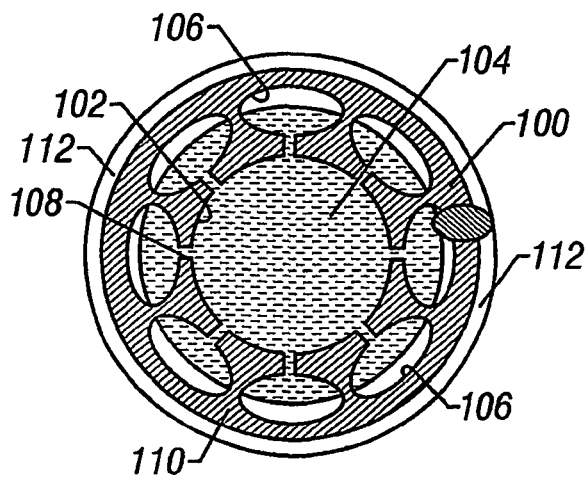
FIG. 8 shows a cross-sectioned view of yet another variation on the tubing for delivering coolant.

FIG. 8 shows another variation for a guidewire coil in the representative cross-section of guidewire 100. As shown, guidewire 100 may have a coolant delivery lumen 102 for transporting coolant 104 within. There may be any predetermined number of heat transfer channels 106 radially disposed around and in fluid communication with delivery lumen 102 through corresponding coolant channels 108. Channels 106 may be located along the length of guidewire 100 at selected locations to optimize the heat transfer at specified locations. As coolant is delivered through delivery lumen 102, it may enter heat transfer channels 106. A conduction member 112 may be embedded within wall 110 such that it contacts the coolant in channels 106 to transfer heat from the outer surface of guidewire 100 to or from the coolant contained within channels 106 to effect ablation. Conduction member 112 is preferably a biocompatible and thermally conductive material such as stainless steel, nitinol, etc. Also, member 112 may be formed in various configurations such as curves, straight lines, etc. over the outer surface of guidewire 100 depending upon the desired range of contact with the surrounding tissue and the area to be cooled or ablated.

Figure 9:
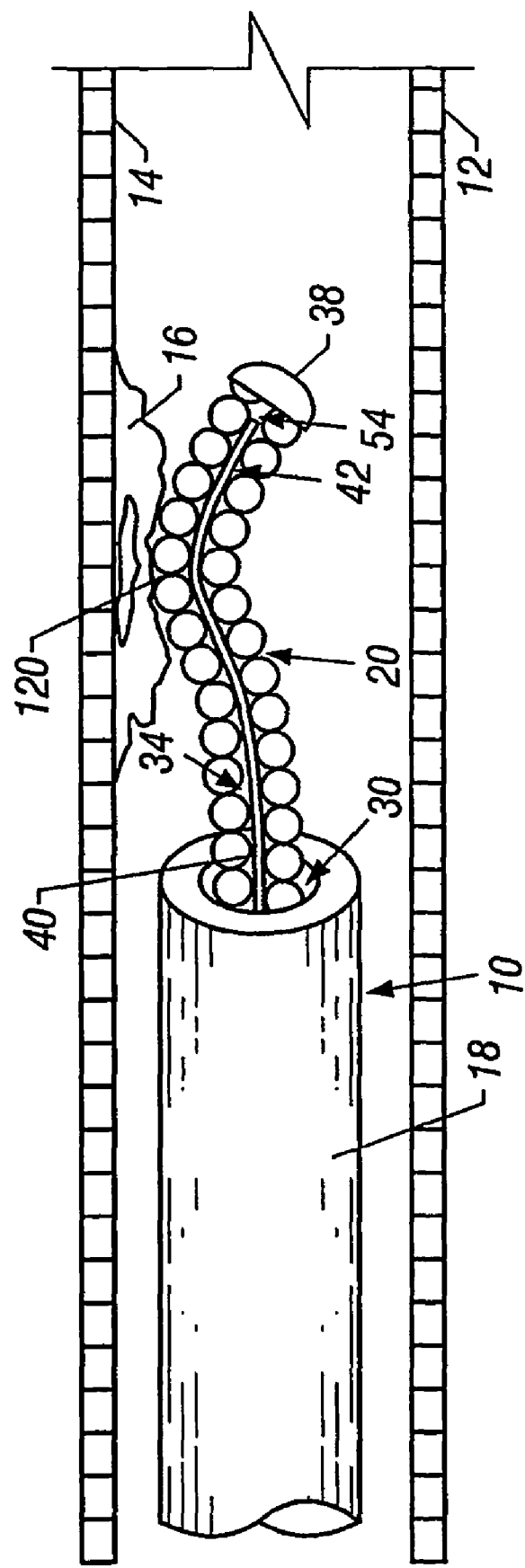
FIG. 9 shows a cross-sectioned side view of a partially withdrawn guidewire contacting a region of tissue to be treated.

FIG. 9 shows a variation of device 10 in operation. As shown, the cross-sectioned guidewire 20 is partially withdrawn from catheter 18 and is reconfigured to a helical configuration within vessel 12, which is also cross-sectioned for clarity. As guidewire 20 reconfigures itself, it may contact the targeted region for treatment, in this case, unstable plaque 16. Guidewire 20 may gently contact plaque 16 at contact region 120, as shown. Once the targeted area of tissue is contacted, coolant may be delivered through delivery tube 40 disposed within guidewire lumen 34. As the coolant passes through delivery ports 42 and/or delivery tube distal end 54, it may flow proximally through guidewire lumen 34 while cooling the guidewire 20, cap 38, and contacted plaque 16 at contact region 120. The tissue at region 120 may be ablated by the cooled guidewire 20 by keeping the temperature between about 35° to 77° F. (20 to 25° C.) for a period of about 1 to 25 minutes. The use of a helically looped guidewire for cooling the tissue allows for the blood flow to remain relatively uninterrupted within the vessel 12 during the treatment time.

Figure 10A:
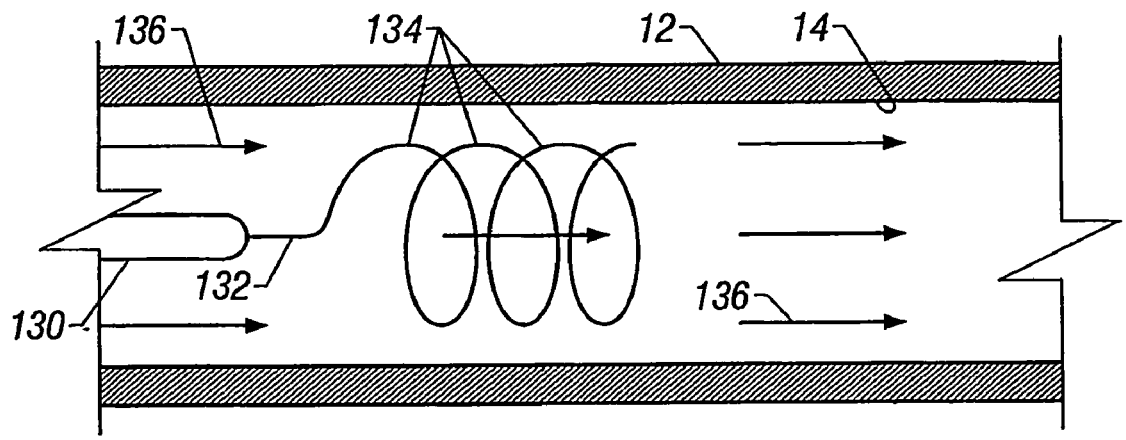
FIGS. 10A to 10C show a variation on the deployment of a cryo-therapy device within a vessel using an angioplasty balloon.
Figure 10B:
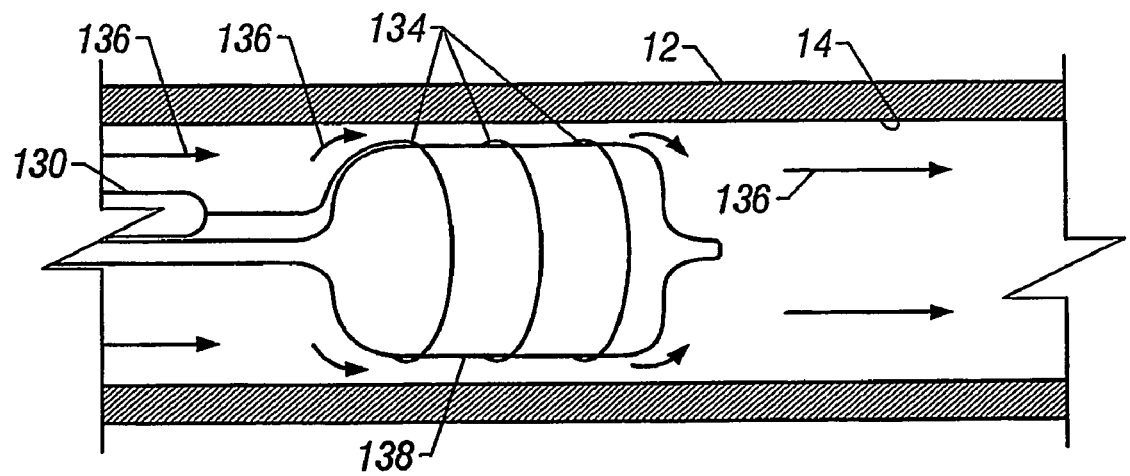
Figure 10C:
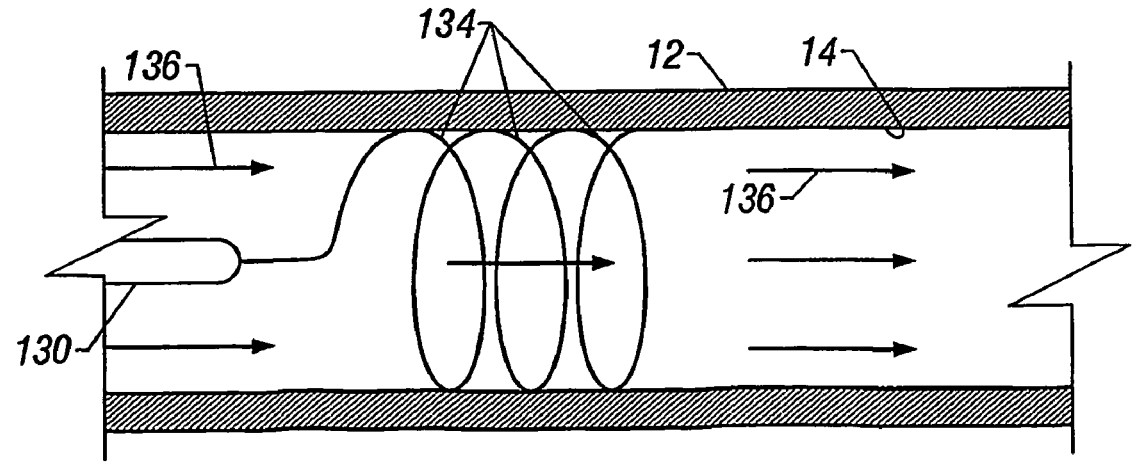

An alternative deployment method may include the use of angioplasty balloons, as seen in FIGS. 10A to 10C, particularly for vessels which may have a relatively wide diameter. FIG. 10A shows cryotherapy device 130 positioned within vessel 12 with hollow guidewire 132 deployed and reconfigured into helical loops 134. To facilitate extending loops 134 radially, an expandable balloon, e.g., angioplasty balloon 138, may be introduced into vessel 12 and inbetween loops 134. Balloon 138 may be introduced separately via another catheter, or it may be introduced through the same catheter through which guidewire 132 is introduced. Once positioned within loops 134, balloon 138 may be expanded slowly to further radially extend loops 134 until they gently contact inner wall 14 of vessel 12, as seen in FIG. 10B. During the expansion of balloon 138, blood flow 136 through vessel 12 may be occluded temporarily until balloon 138 is collapsed. Once loops 134 are in gentle contact with inner wall 14, balloon 138 may be removed and treatment to the tissue may occur, as described above. FIG. 10C shows loops 134 contacting inner wall 14 with blood flow 136 resumed.

Figure 11:
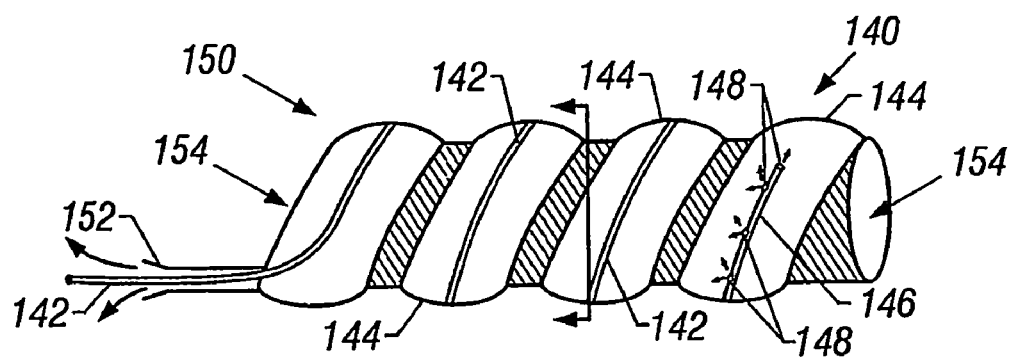
FIG. 11 shows a variation on the cryo-therapy device in which the coolant delivery tube is helically disposed within an expandable bilayered balloon.

Another variation for deploying a helically-shaped coolant delivery tube is shown in FIG. 11. This variation employs a bilayered expandable balloon 140 having a helically wound coolant delivery tube 142 disposed within a helical coolant return channel 144. Coolant delivery tube 142 preferably releases coolant near the tube distal end 146 through delivery ports 148 which flows back proximally towards balloon proximal end 150 through return channel 144 and through coolant return lumen 152. During deployment, balloon 140 may be in a deflated state until it is positioned at the tissue to be treated. Balloon 140 may then be inflated such that return channel 144 contacts the tissue and coolant may be pumped into delivery tube 142 such that the tissue contacting balloon 140 is cooled or ablated. It may be desirable to maintain blood flow through the vessel in which balloon 140 is treating tissue, thus a throughpath 154 may be defined through balloon 140 to facilitate such a blood or fluid flow path when balloon 140 is in an expanded state.

Figure 12:
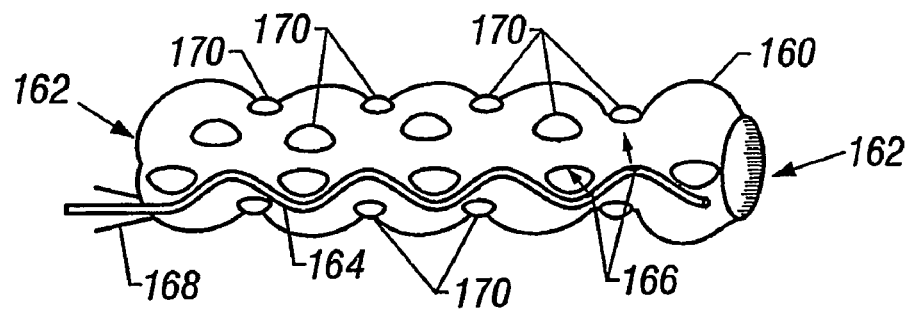
FIG. 12 shows another variation on the cryo-therapy device in which the coolant delivery tube is disposed within an expandable balloon having embedded conduction contacts.

In addition to the expandable balloon 140 in FIG. 11, another variation on an expandable balloon 160 is seen in FIG. 12. Balloon 160 may also define a throughpath 162 throughout the device for facilitating blood or fluid flow through the balloon 160 for when it is in an expanded state within a vessel lumen. This variation shows coolant delivery tube 164 disposed within balloon 160. Any number of conduction contacts 170 may be embedded within the surface of balloon 160 to effect optimal conductive heat transfer. Contacts 170 are preferably made of a biocompatible metal which is thermally conductive, e.g., stainless steel, nitinol, etc. When coolant is pumped into the balloon 160 through coolant ports 166, the coolant may spread throughout balloon 160 and thermally conduct heat through contacts 170 from the contacting tissue wall before being drawn through coolant return lumen 168.

Figure 13:
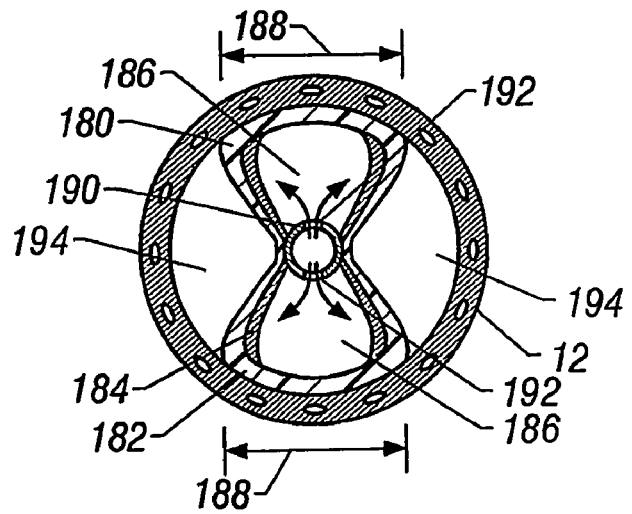
FIG. 13 shows a representative cross-section of a variation on the cryo-therapy device having an expandable flowthrough balloon.

FIG. 13 shows a representative cross section of one variation on an expandable flowthrough balloon 180 which may be used with a number of variations. Balloon 180 is shown in cross section disposed within vessel 12. This variation may have an expandable membrane configured to expand in at least two directions. A coolant delivery tube 190 may be located within the expandable membrane which may be made of thinned membranes 182 for contacting vessel 12 and insulative membranes 184 which may insulate the coolant from blood and fluids passing through flow channel 194. As coolant is passed through delivery tube 190, the coolant may flow through delivery ports 192 and expand into expansion region 186. As more coolant flows into region 186, the membrane may expand and contact vessel 12 at thinned membranes 182 creating conductive regions 188. Although this variation shows two opposed expanding regions, any number of expandable areas may be implemented depending upon the desired effect and area for cooling.

Figure 14:
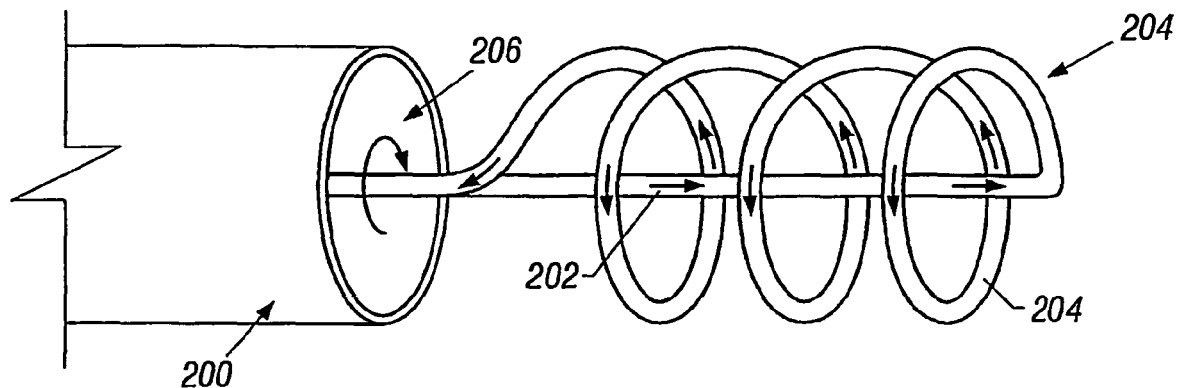
FIG. 14 shows another variation on the cryo-therapy device in which the helical loops are in fluid communication with a translatable and rotatable coolant delivery stem.

A further variation on having a helically shaped cooling guidewire or coil is shown in FIG. 14. Delivery catheter 200 may have a rotatable coolant delivery stem 202 which may be withdrawn from lumen 206. A number of helically wound loops 204 in fluid communication with a distal end of delivery stem 202 may wind about stem 202 to transport coolant back towards a proximal end of catheter 200. In operation, catheter 200 may be advanced within a vessel to a treatment site. Both stem 202 and loops 204 may be withdrawn from catheter 206 and loops 204 may be allowed to extend radially so that they come into contact with the tissue. Coolant may then be delivered through delivery stem 202 and back through loops 204 to effect treatment to the tissue contacting loops 204, as described above. Stem 202 and loops 204 may be independently rotatable and translatable relative to catheter 200 to enable effective placement of the device. Once treatment is concluded, stem 202 and loops 204 may be withdrawn back into catheter lumen 206 and removed from the region.

Figure 15A:
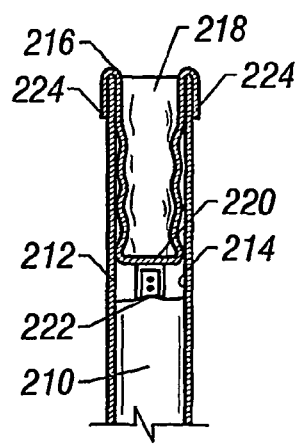
FIGS. 15A and 15B show yet another variation on the cryo-therapy device in which an expandable balloon may be disposed within the guidewire lumen prior to deployment.
Figure 15B:
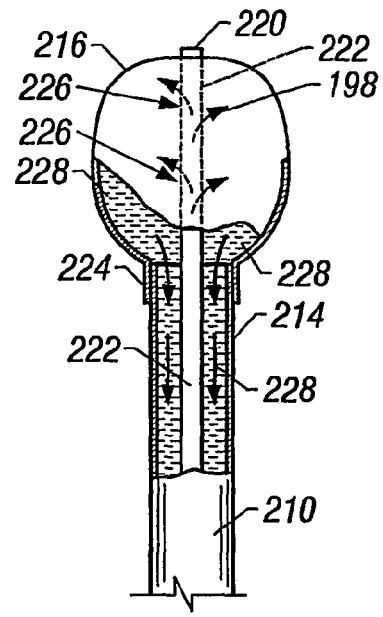

Another variation on an expandable balloon is shown in FIGS. 15A and 15B. This variation may be disposed at the end of any of the helically wound guidewires described above to effect localized treatment at the distal end of the guidewire. Alternatively, this variation may also be utilized independently to cool or ablate tissue. FIG. 15A shows hollow guidewire 210 having an everted and deflated balloon 216 withdrawn proximally within guidewire lumen 214 and creating recessed cavity 218. The end of balloon membrane 216 is preferably attached to guidewire walls 212 at balloon attachment region 224. Coolant delivery tube 222 may be seen attached at its distal end to the end of balloon membrane 216 at attachment point 220. After guidewire 210 is radially extended into helical loops and is adjacent to the region of tissue to be treated, as described above, stem 222 may be advanced distally. Advancing stem 222 forces balloon membrane 216 to evert because of attachment point 220 and withdraws membrane 216 from recessed cavity 218. Once balloon membrane 216 has been extended, coolant may be delivered through stem 222 and passed through delivery ports 226 into balloon membrane 216. The coolant may then force balloon membrane 216 to expand, as shown in FIG. 15B, causing membrane 216 to contact the tissue wall for treatment. The spent coolant may then return proximally through return channel 228.

Figure 16:
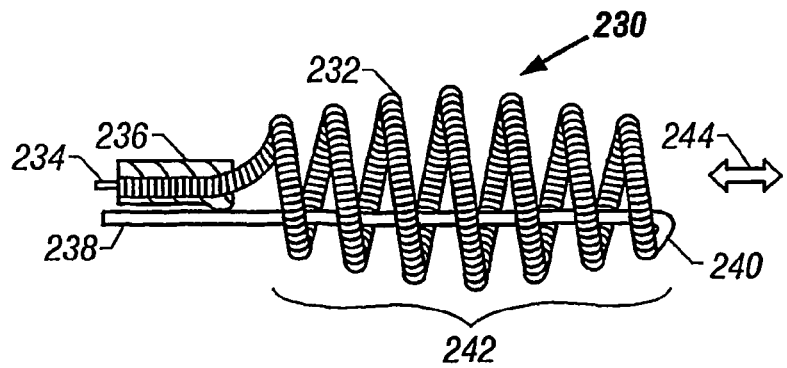
FIG. 16 shows yet another variation on the cryo-therapy device in which the helically looped guidewire may be longitudinally variable.

FIG. 16 shows another variation in which the helically looped guidewire may be longitudinally variable. Collapsible guidewire device 230 is shown as having coolant delivery tube 234 disposed within guidewire 232, as in some of the other variations above. A portion of guidewire 232 may be partially insulated with insulation 236 and control member 238 may be positioned longitudinally within the loops of guidewire 232. The distal end of member 238 may be attached to the distal tip of guidewire 232 at attachment point 240. Control member 238 may be a wire or stiff member and is preferably manipulated at its proximal end to move guidewire 232 in the direction of movement shown by arrow 244 to variably collapse or expand device 230 longitudinally. This variability in longitudinally contracting or expanding device 230 creates a collapsible region 242 in which the loops of guidewire 232 may be concentrated or dispersed to control the heat transfer area contacting the targeted tissue.

The applications of the cryo-therapy devices discussed above are not limited to endovascular treatments but may include any number of further treatment applications. Other treatment sites may include areas or regions of the body such as organ bodies or spaces between the body cavity. Modification of the above-described assemblies and methods for carrying out the invention, and variations of aspects of the invention that are obvious to those of skill in the art are intended to be within the scope of the claims.

I claim:

1. An apparatus for thermally treating a hollow body organ comprising:
    a catheter having a proximal end and a distal end and defining at least one lumen therebetween;
    a guidewire comprised of a helically coiled structure which defines at least one passageway therethrough, wherein the guidewire has a free distal end projecting distally from the catheter lumen and is configured to have a first configuration when disposed within the lumen and a second radially extended configuration when withdrawn from the lumen such that the second configuration defines a plurality of helical loops formed by the coiled structure and which extend along a longitudinal axis which is coincident with a longitudinal axis of the catheter;
    a delivery tube disposable within the guidewire passageway for transporting a fluid, wherein the delivery tube defines at least one exit port near a distal end of the delivery tube through which the fluid passes; and,
    a membrane separate from the guidewire and disposed along the at least one passageway for containing the fluid therein.

2. The apparatus of claim 1 further comprising a cap disposed over the distal end of the guidewire.

3. The apparatus of claim 2 wherein the cap comprises a thermally conductive material.

4. The apparatus of claim 1 further comprising a plurality of insulative barriers attached to an, outer surface of the guidewire.

5. The apparatus of claim 1 further comprising an elongate control member having a proximal end and a distal end, wherein the distal end of the control member is attached to the distal end of the guidewire such that the guidewire is manipulatable along a longitudinal axis defined by the catheter via a proximal end of the elongate member.

6. The apparatus of claim 1 wherein the guidewire is configured to self-form from the first configuration to the second larger configuration.

7. The apparatus of claim 1 wherein the guidewire comprises a superelastic metal.

8. The apparatus of claim 1 wherein the helical loops are configured to extend radially into contact with the hollow body organ.

9. The apparatus of claim 1 wherein the delivery tube defines a plurality of additional exit ports near the distal end.

10. The apparatus of claim 9 wherein each of the additional exit ports has a diameter which increases in size the farther distally the exit port is located.

11. The apparatus of claim 1 wherein the delivery tube further comprises a valve positioned at the exit port.

12. The apparatus of claim 1 wherein the delivery tube distal end is anchored at a distal end of the guidewire.

13. The apparatus of claim 1 wherein the delivery tube is integrally formed within the guidewire passageway.

14. The apparatus of claim 1 wherein the fluid comprises a liquid or gas coolant.

15. The apparatus of claim 14 wherein the fluid comprises a coolant selected from the group consisting of nitrogen, nitrous oxide, carbon dioxide, saline, fluorinated hydrocarbon, and chlorodifluoromethane.

16. The apparatus of claim 1 wherein the fluid is in a liquid phase in the delivery tube and in a gaseous phase when passed through the exit poll.

17. The apparatus of claim 1 further comprising a pump in fluid communication with the delivery tube at a proximal end of the tube.

18. An apparatus for thermally treating a hollow body organ comprising:
 a catheter having a proximal end and a distal end and defining at least one lumen therebetween;
 a hollow tubular member comprised of a helically coiled structure which defines at least one passageway therethrough, wherein the hollow tubular member has a free distal end projecting distally from the catheter lumen and is configured to have a first configuration when disposed within the lumen and a second radially extended configuration when withdrawn from the lumen such that the second configuration defines a plurality of helical loops formed by the coiled structure and which extend along a longitudinal axis which is coincident with a longitudinal axis of the catheter;
 a delivery tube disposable within the tubular member passageway for transporting a fluid, wherein the delivery tube defines at least one exit port near a distal end of the delivery tube through, which the fluid passes; and,
 a membrane separate from the tubular member and disposed along the at least one passageway for containing the fluid therein.

19. The apparatus of claim 18 further comprising a cap disposed over the distal end of the tubular member.

20. The apparatus of claim 19 wherein the cap comprises a thermally conductive material.

21. The apparatus of claim 18 further comprising a plurality of insulative barriers attached to an outer surface of the tubular member.

22. The apparatus of claim 18 further comprising an elongate control member having a proximal end and a distal end, wherein the distal end of the control member is attached to the distal end of the tubular member such that the tubular member is manipulatable along a longitudinal axis defined by the catheter via a proximal end of the elongate member.

23. The apparatus of claim 18 wherein the tubular member is configured to self-form from the first configuration to the second larger configuration.

24. The apparatus of claim 18 wherein the tubular member comprises a superelastic metal.

25. The apparatus of claim 18 wherein the helical loops are configured to extend radially into contact with the hollow body organ.

26. The apparatus of claim 18 wherein the delivery tube defines a plurality of additional exit ports near the distal end.

27. The apparatus of claim 26 wherein each of the additional exit ports has a diameter which increases in size the farther distally the exit port is located.

28. The apparatus of claim 18 wherein the delivery tube further comprises a valve positioned at the exit port.

29. The apparatus of claim 18 wherein the delivery tube distal end is anchored at a distal end of the tubular member.

30. The apparatus of claim 18 wherein the delivery tube is integrally formed within the tubular member passageway.

31. The apparatus of claim 18 wherein the fluid comprises a liquid or gas coolant.

32. The apparatus of claim 31 wherein the fluid comprises a coolant selected from the group consisting of nitrogen, nitrous oxide, carbon dioxide, saline, fluorinated hydrocarbon, and chlorodifluoromethane.

33. The apparatus of claim 18 wherein the fluid is in a liquid phase in the delivery tube and in a gaseous phase when passed through the exit port.

34. The apparatus of claim 18 further comprising a pump in fluid communication with the delivery tube at a proximal end of the tube.

35. The apparatus of claim 1 wherein at least a portion of the guidewire is comprised of a wire wound into the helically coiled structure such that the helical coils are adjacent to one another.

36. The apparatus of claim 18 wherein the at least a portion of the hollow tubular member is comprised of a wire wound into the helically coiled structure such that the helical coils are adjacent to one another.

\* \* \* \* \*